(12) United States Patent
Briggs et al.

(10) Patent No.: US 7,863,590 B2
(45) Date of Patent: Jan. 4, 2011

(54) UV IRRADIATOR

(75) Inventors: David Briggs, Reading (GB); Richard Little, Southampton (GB)

(73) Assignee: JenAct Limited, Whitchurch, Hampshire (GB)

( * ) Notice: Subject to any disclaimer, the term of this patent is extended or adjusted under 35 U.S.C. 154(b) by 176 days.

(21) Appl. No.: 12/190,658

(22) Filed: Aug. 13, 2008

(65) Prior Publication Data
US 2009/0045356 A1 Feb. 19, 2009

(30) Foreign Application Priority Data
Aug. 15, 2007 (GB) .................................. 0715915.5

(51) Int. Cl.
H01J 21/33 (2006.01)
A61L 2/10 (2006.01)
A61N 5/06 (2006.01)

(52) U.S. Cl. ................ 250/504 R; 250/455.1; 250/461.1; 250/365; 315/39; 315/157

(58) Field of Classification Search ............ 250/504 R, 250/455.1, 461.1, 365; 315/39, 157
See application file for complete search history.

(56) References Cited

U.S. PATENT DOCUMENTS

| 4,933,602 A | 6/1990 | Ono et al. |
| 6,693,382 B2 * | 2/2004 | Little et al. ................. 315/157 |
| 6,856,093 B2 * | 2/2005 | Little et al. ................... 315/39 |
| 7,566,890 B2 * | 7/2009 | Briggs et al. ............ 250/504 R |
| 2009/0045750 A1 * | 2/2009 | Briggs et al. ................. 315/157 |

FOREIGN PATENT DOCUMENTS

| GB | 2413005 A | 10/2005 |
| GB | 2399216 B | 5/2007 |
| RU | 2280617 C1 | 7/2006 |
| WO | 2004/088706 A3 | 10/2004 |
| WO | 2006/103287 A3 | 11/2006 |
| WO | 2007048417 A1 | 3/2007 |

* cited by examiner

Primary Examiner—Nikita Wells
(74) Attorney, Agent, or Firm—Fox Rothschild LLP; Alexis Barron

(57) ABSTRACT

An apparatus having one or more UV bulbs arranged around a structural element and within an outer conductive element. The apparatus also contains an inner conductive element which extends the length of the apparatus. The inner and outer conductive elements are coupled to a microwave source to enable the UV bulbs to be powered.

20 Claims, 1 Drawing Sheet

UV IRRADIATOR

FIELD OF THE INVENTION

This invention relates to a UV light irradiation system which is particularly, though not exclusively, suitable for submerged use in fluids or gases for the purpose of, for example, water or air purification, disinfection, sanitisation or other treatment. The irradiation being energised by microwave energy.

BACKGROUND OF THE INVENTION

UV light is used for many different purposes including, for example, the use of UVC irradiation for the purification or other treatment of fluids such as air or water. U.S. Pat. No. 6,693,382 entitled "Control system for microwave powered light sources" discloses that there is a maximum desirable power density for UVC emitting electrodeless light sources. There is also a maximum desirable bulb diameter to prevent reabsorbtion of UVC generated by a plasma core which will make the system inefficient at outputting UVC light. It is, therefore, often advantageous to maximise the amount of energisable plasma per unit of irradiator length by the use a plurality of UV bulbs in parallel.

In existing systems, such as that described in GB 2 399 216, when a plurality of bulbs are used in a single irradiator light source, light from each bulb is emitted evenly over it's circumference and, thus, part of each bulb's emission will be transmitted onto, and absorbed by, other adjacent bulbs and, thus, not all the light outputted from the bulb can be used to irradiate the fluid. Additionally, the power density of the neighbouring bulbs is also disturbed. Hence, the power per bulb length output is limited as some of the power is reabsorbed by neighbouring bulbs.

GB 2 413 005 describes an improved radiator where the centre conductor may be reflective and therefore may redirect some of the light that would otherwise be absorbed by adjacent bulbs out of the irradiator. However, the necessary shape of the centre conductor limits its ability to reflect all the light incident upon it. Additionally, if the structure is powered by microwaves from one end only it is difficult to evenly energise the bulbs within the irradiator along their entire length.

The present invention provides apparatus including an inner conductive element, a structural element, an outer conductive element and at least one bulb configured to emit light in response to microwaves. The outer conductive element is substantially transmissive to light. The structural element forms conductive cavities that are preferably longitudinal. The bulb is positioned within one of the cavities within the outer conductive element. The inner and outer conductive elements are coupled to a microwave source in such a way that the inner conductive element acts as the centre conductor of a coaxial transmission system and the outer conductive element acts as the outer conductor of the coaxial transmission system.

The structural element is preferably also conductive; thereby acting in conjunction with the outer conductive element to form an outer conductor of subsidiary coaxial systems that are formed within the cavities of the irradiator.

It is preferable that the structural element includes a bore that extends through it and through which the inner conductive element can pass from one end of the irradiator to the other.

The apparatus may be further provided with at least one chamber, but preferably two or more. The one or more chambers may be defined either by an end plate of the irradiator and the end of a section of the structural element. Alternatively, the one or more chambers may be defined by a space between two sections of inner structural element. The inner conductor extends through the chambers, and hence, a microwave cavity is created in each cavity between the outer conductive element which extends over the outside of the chamber and the inner conductive element. The elements being connected to and energised by a suitable microwave source.

Preferably, the apparatus is provided with a plurality of bulbs and the structural element is configured to provide an equal number of cavities to the number of bulbs. The bulbs extend through the cavities and at least partially into the chamber or chambers present in the apparatus.

Typically, the UV bulbs are electrodeless. Preferably, the UV bulbs have a diameter of less than 22 mm and are constructed of UVC transmissive quartz. Preferably, they contain a mixture of Argon and Mercury such that, when exposed to microwave radiation at approximately 2.45 GHz they illuminate and irradiate at the Mercury based UV spectra.

As described above, the chambers will energise the plasma in the parts of the bulb that extend into the chambers. As microwave induced plasmas such as those described above act as lossy conductors, the energisation of the plasma will extend along the longitudinal cavity with the UV bulb acting as the central conductor within the cavity. Thus, the cavities encompassed as they are by the outer conductive element and structural element form subsidiary coaxial transmission systems.

Hence, this structure enables a plurality of bulbs in cavities around a structural element can be more evenly energised by microwave energy present in the chambers.

Preferably, the surface of the cavities is reflective and optimised the maximise the UV emissions from the bulbs through the outer conductive element.

The microwave source may be introduced directly to a chamber at one end of the irradiator. Alternatively, it may be connected via a waveguide or co-axial line where the central conductor of the coaxial line is connected to the inner conductive element of the irradiator and the outer conductor of the coaxial line is connected to the outer conductive element.

Preferably, the structural is a solid electrical conductor. Preferably, the structural element is constructed from aluminium extrusion with a reflective polished outer surface extending up to the junction between an edge of the structural element and outer conductive element. This reduces the amount of light emitted by a bulb being intercepted by any other bulbs in the system.

The inner conductive element is preferably a metallic rod. The inner conductive element preferably passes through the bore of the structural element and, thus, this acts as a coaxial transmission line transmitting microwave energy from the source input to the chambers in the irradiator. This allows the bulbs within the irradiator to be energised at multiple points along their length.

Preferably, pressurised air can be passed through the space between the inner conductive element and the bore of the structural element. The air can return through the longitudinal cavities thereby cooling the bulbs or allowing the creation of ozone.

The apparatus may include a UV transmissive fluid-tight envelope arranged around the outer conductor which allows the generator to operate whilst immersed in a fluid such as water. Preferably, the envelope may be formed from quartz.

Preferably, the apparatus includes a spark generator arranged to generate a spark through or adjacent the bulb or bulbs in order to encourage ignition of the bulb or bulbs.

BRIEF DESCRIPTION OF THE DRAWINGS

Other aspects and features of the present invention will become apparent to those ordinarily skilled in the art upon review of the following description of specific embodiments of the invention in conjunction with the accompanying figures.

DETAILED DESCRIPTION

In the present application, irradiator is used to denote any light system which produces a light emission in response to microwave energisation.

Figure 1:
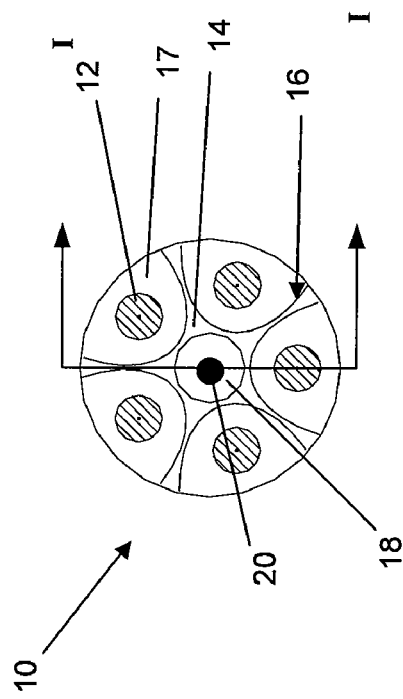
FIG. 1 illustrates a cross-section through the light system of the present invention.

With reference to FIG. 1, the irradiator 10 includes a plurality of UV light bulbs 12 arranged around a structural element 14. The structural element 14 has a plurality of concave surfaces 16 which form longitudinal cavities each cavity 17 being arranged to receive one UV bulb 12. The surfaces 16 of the longitudinal cavities act to reflect light emitted from the UV light bulbs 12 and to prevent light emitted by a bulb 12 being transmitted onto, and absorbed by, adjacent bulbs 12.

The structural element 14 is further provided with a hollow bore ('core') 18 forming a path that runs through the centre of the structural element 14.

An inner conductive element 20 passes through the bore 18. The inner conductive element 20 acts as the central conductor for a primary coaxial structure.

Additionally, cooling air or any other fluid can be moved through the central bore 18 such that it can circulate through the irradiator 10. Preferably, the air circulates through the bore 18 of the structural element 14 and then back over the UV light bulbs 12 thereby promoting cooling of the system.

Figure 2:
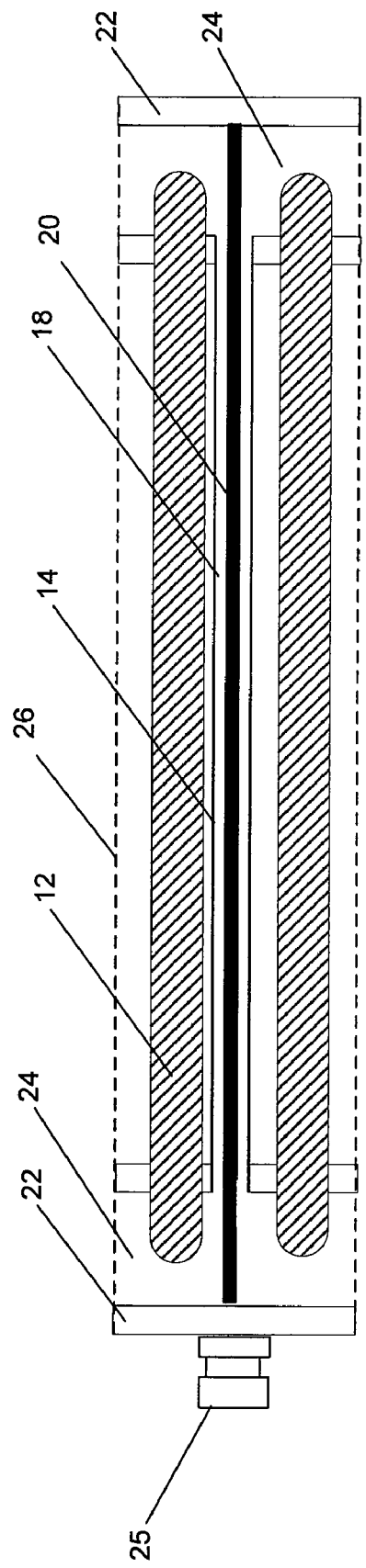
FIG. 2 is a sectional view along the line I-I of FIG. 1.

With reference to FIG. 2, end plates 22 are positioned at either end of the light system. The structural element 14 terminates a distance away from the end plates 22 thereby forming an end chamber 24 at each end of the UV light bulbs 12. The end of the structural element is provided with a support to support the UV bulbs 12 in place above the structural element 14. Additional holes (not shown) in the support can be present to enable the passage of cooling fluids, etc., through the light system.

A microwave source is coupled to one of the end chambers 24, for example, at 25. The microwave source supplies microwaves into the light system. The microwaves then travel down the bore 18 of the inner structural element 14 until they reach the second end chamber. In this way, the microwaves can reach both end chambers. Hence, the electrodeless UV light bulbs can be energised at both ends, thereby enabling a more even distribution of UV emissions from each of the UV bulbs in the light system.

A coaxial outer 26 is formed around the outer circumference of the light system 10 by virtue of an outer conductive element. The coaxial outer 26 is made from an electrically conductive material such that it can contain an electromagnetic field and allow transmission of light in the UV spectrum. The outer conductive element 26 is preferably made from a reticulated material such as electrically conductive mesh or from a perforated conductive material.

In use, microwaves are introduced into an end chamber 24. The UV light bulbs are electrodeless bulbs that emit UV light upon exposure to microwaves.

Optionally, the structural element may be provided with slots in its outer surface between the two end chambers. These slots allow microwaves to be transmitted from the central core to the radial coaxial cavities so that the bulbs can be further energised at intermediate points along their length. Hence, more even energisation of the bulbs can be achieved. Hence, the length of the system, the evenness of the microwave power absorption and irradiator UV emission can be increased as the points at which UV light bulbs are increased.

The system may be encased in a fluid-tight envelope (not shown) which allows the arrangement to be submerged in water, for example. Preferably, the envelope is UV transmissive (quartz being a typically good material for its construction). This may permit water-cooling of the magnetron and bulbs at the same time as allowing sterilisation of the surrounding water. The magnetron attached to the end chamber may be immersed directly in water, enclosed in a separate enclosure which may, for example, be oil filled to aid heat transmission, or it may be in the fluid-tight envelope with the bulb. As a further alternative, the magnetron may remain out of the water and be air or water cooled in the normal way.

The structural element is preferably made from a polished conductor that promotes reflection of the UV light and thus maximises UV emissions from the irradiator. For example, it may be made from polished aluminium. The structural element may, for example, be shaped as described above. Alternatively, it may take any other suitable shape, for example, be round, triangular or square in cross-section.

The bore through the inner structural element may also be of any suitable shape cross section and take any suitable path through the inner conductor.

It is preferable that the structural element is a continuous metal/conductive structure made by, for example, extrusion of a metal or any other known method. This enables the outer conductive element acting as a coaxial outer to be formed of a weaker material, for example, the holes in reticulated material may be enlarged to improve UV transmission through the outer conductive element.

The supports present at either end of the structural element may be made from any suitable material, for example, PTFE.

What is claimed is:

1. Apparatus including:
    a) a plurality of bulbs configured to emit light when energised by microwaves;
    b) an outer conductive element which is at least partially transmissive to UV light;
    c) an inner conductive element situated within the outer conductive element;
    d) a structural element situated within the outer conductive element and including a plurality of cavities, each bulb being situated within a separate cavity;
    e) a chamber characterised by formed within the outer conductive element and at least one of which is defined by an end of the structural element, the bulb and inner conductive element extending into the chamber; and
    f) the apparatus arranged that such that when the apparatus is exposed to microwaves from the microwave source the inner and outer conductive elements act to energise the bulbs.

2. Apparatus according to claim 1 wherein the chamber is defined at one end by an end plate of the apparatus and at the other by an end of the structural element.

3. Apparatus according to claim 1 wherein the apparatus is provided with a second chamber defined at one end by the other end plate of the apparatus and at the other by the other end of the structural element.

4. Apparatus according to claim 1 wherein the apparatus includes a further intermediate chamber wherein the chamber is defined by a gap within the structural member.

5. Apparatus according to claim 1 wherein at least one of the chambers is directly coupled to a microwave source.

6. Apparatus according to claim 1 wherein at least one of the chambers is indirectly coupled to a microwave source.

7. Apparatus according to claim 1, wherein the structural element is an electrical conductor.

8. Apparatus according to claim 1 wherein either end of the structural member is provided with a support to support the bulbs above the structural member.

9. Apparatus according to claim 1 wherein the surface of the cavities of the structural element are polished or lined with a polished material.

10. Apparatus according to claim 1 wherein the structural element is arranged to provide a distinct focussed, reflective surface for the or each bulb.

11. Apparatus according to claim 1 wherein the apparatus is longitudinal.

12. Apparatus according to claim 1 wherein the bulbs and cavities are positioned radially about the central axis of the apparatus.

13. Apparatus according to claim 1 wherein the structural element is provided with a bore and the inner conductive element extends through the bore.

14. Apparatus according to claim 1 wherein the light emitted by the bulbs is UV light.

15. Apparatus according to claim 1 including a UV transmissive fluid-tight envelope arranged around the outer conductor which allows the generator to operate whilst immersed in a fluid such as water.

16. Apparatus according to claim 15, wherein the envelope is formed from quartz.

17. Apparatus according to claim 1 including a spark generator arranged to generate a spark through or adjacent a bulb in order to encourage ignition of the bulb.

18. Apparatus according to claim 1 including a wire having a high melting point arranged to generate a spark through or adjacent a bulb in order to encourage ignition of the bulb.

19. Apparatus according to claim 18 wherein the wire is made from tungsten.

20. Apparatus according to claim 1 including a UV lamp in proximity to a bulb in the apparatus the UV lamp acting as an igniter bulb.

* * * * *